United States Patent
Rothschild et al.

(10) Patent No.: US 6,497,028 B1
(45) Date of Patent: Dec. 24, 2002

(54) METHOD FOR CONSTRUCTING A PROSTHESIS

(75) Inventors: Vernon R. Rothschild, Berlin, MD (US); John R. Fox, Trappe, MD (US); Russell J. Rothschild, Chester, MD (US); Kelly Ann Rothschild, Berlin, MD (US)

(73) Assignee: Rothschild's Orthopedics, Inc., Salisbury, MD (US)

( * ) Notice: Subject to any disclaimer, the term of this patent is extended or adjusted under 35 U.S.C. 154(b) by 33 days.

(21) Appl. No.: 09/702,131

(22) Filed: Oct. 31, 2000

(51) Int. Cl.⁷ .................................................. A61F 2/60
(52) U.S. Cl. .............................. 29/416; 29/423; 29/460; 623/27; 623/32; 623/33
(58) Field of Search ......................... 29/416, 423, 424, 29/458, 460, 469, 527.1, 527.2, 557, 407.09; 623/27, 32, 33

(56) References Cited

U.S. PATENT DOCUMENTS

| | | | |
|---|---|---|---|
| 4,314,398 A | 2/1982 | Pettersson | |
| 4,395,783 A | 8/1983 | Eyre et al. | |
| 5,004,477 A | * 4/1991 | Palfray | 623/27 |
| 5,152,800 A | 10/1992 | Rothschild et al. | |
| 5,219,364 A | 6/1993 | Lloyd | |
| 5,226,918 A | * 7/1993 | Silagy et al. | 623/27 |
| 5,336,270 A | * 8/1994 | Lloyd | 623/33 |
| 5,503,543 A | * 4/1996 | Laghi | 623/27 |
| 5,880,964 A | * 3/1999 | Schall et al. | 623/27 |
| 5,993,487 A | 11/1999 | Skardoutos et al. | |

* cited by examiner

Primary Examiner—David P. Bryant
Assistant Examiner—Jermie E. Cozart
(74) Attorney, Agent, or Firm—Nixon Peabody LLP; Donald R. Studebaker

(57) ABSTRACT

Improved prosthetic components and a method for assembly therefor are described wherein the prosthesis comprises prefabricated modular components including a socket adapter, shank or pylon, a keel, and a foot. The method for preparation of the improved prosthesis reduces the time required for prosthesis preparation over that of the prior art, and includes the steps of making a cast of the remaining leg stump and forming a socket therefor; placing the socket in an alignment jig; assembling modular pieces including a prefabricated keel, pylon, and socket adapter; attaching the socket adapter to the socket; draping a final coating of copolymer on the prosthesis; and removing the pylon and socket adapter from the interior of the prosthesis.

10 Claims, 1 Drawing Sheet

METHOD FOR CONSTRUCTING A PROSTHESIS

BACKGROUND OF THE INVENTION

1. Field of the Invention

This invention is directed to artificial prosthetic components and assembly methods therefor for use in a human lower limb prosthesis. More particularly, this invention is directed to improved human prostheses and methods therefor wherein the prosthesis comprises modular prefabricated components.

2. Description of Related Art

The most common artificial leg for below knee amputees is of a rigid nature. A solid shank connects the socket, which mounts the artificial leg to the residual limb of the amputee, and the artificial foot. The shank is often made out of a rigid alloy, such as one containing titanium, or from shaped wood or plastic. It can be solid for strength, or it can be hollow for lightness.

In a typical conventional prosthesis fabrication technique, a significant amount of time and effort is wasted in duplicating fabrication steps. Generally, conventional fabrication includes taking a cast of the patient's stump and making a socket incorporating the necessary fittings, including (a) an alignment fitting for angular adjustments; (b) a tubular fitting for length and rotational adjustment; (c) a fitting for linear adjustments; and (d) an ankle fitting for angular adjustments and to allow attachment of a foot. The prosthesis is assembled for bench alignment and the patient is scheduled for dynamic alignment. When the patient and prosthesis are satisfied with both the fit of the socket and the alignment of the prosthesis, the prosthesis is duplicated in an alignment device that captures the prosthetic alignment and allows removal of the metal components and replacing them with polyurethane. The area between the top of the keel and the bottom of the socket is foamed in place, and when the foam hardens, the shank is hand shaped to the desired configuration between the keel and the socket. The prosthesis is prepared for the final draping of copolymer plastic. If the finished prosthesis is not satisfactory and can not be adjusted, the process is repeated using the same components. The approximate fabrication time for this procedure is 5 to 8 hours.

As an example, U.S. Pat. No. 4,314,398 discloses a method of making a lower leg prosthesis comprising the steps of (a) forming a temporary prosthesis socket having an inner shape corresponding to the remaining lower leg stump of the amputee to which the prosthesis is to be attached; (b) forming a test prosthesis by fixing an adjustable position testing device to the temporary socket and connecting the testing device to the prosthesis foot through a temporary connecting member; (c) testing the test prosthesis on the patient and adjusting the testing device so as to obtain a proper alignment of the temporary socket in relation to the prosthesis foot; (d) providing a positive prosthesis socket in the temporary socket of the test prosthesis and reproducibly fixing the assembly comprised of the positive socket, the temporary socket, the testing device and at least the temporary connecting member in a support device; (e) removing the test prosthesis parts from the support device; (f) placing the connecting member adjacent the positive socket in the support device in the aligned relative position reproducibly set in the support device in step (d); and (g) forming the prosthesis socket on the positive socket while simultaneously securing the connecting member to the prosthesis socket in the aligned relationship thereby obtaining an individually aligned lower leg prosthesis. However, the method associated with this reference requires duplicating assembly steps; i.e., fixing the adjustable position testing device to a temporary socket and temporarily connecting this device to the prosthesis foot, followed by removing the test prosthesis and replacing it with a permanent member in the position formerly occupied by the testing device.

U.S. Pat. No. 5,152,800 discloses a below the knee prosthesis and method for making the same. The prosthesis includes a socket for receiving the stump of the below-the-knee amputee, a keel having a peripheral groove formed about the periphery of a bottom portion of the keel, a tubular shin member extending from the socket and surrounding lateral and medial portions of the keel and filling the peripheral grooves formed about the bottom portion of the keel leaving a substantial portion of the bottom of the keel exposed. A resilient foot member is then secured to the exposed portion of the keel with the material of the tubular shin member being formed into the grooves of the keel and maintaining such keel within the shin member. The method thereof includes the steps of forming a socket for receiving a stump of the below-the-knee amputee; constructing a shin support about the socket including an ankle block and keel about the socket in accordance with the size and stature of the amputee; forming a retaining means in a bottom surface of the keel for retaining the keel in a predetermined position with respect to the socket; molding a sheet of copolymer material about the shin support, into the retaining means and over the bottom surface of the keel to form a shin member; removing the copolymer material from the bottom surface of the keel; removing a substantial portion of material used to construct the shin support from within the shin member; and securing a foot member to the keel. The method for assembly of this device does not take advantage of a prefabricated socket adapter/pylon/keel assembly, instead requiring several distinct steps for assembling the prosthesis including assembling a shin support between the socket adapter and the keel, foaming the support, draping a copolymer exterior on the assembly, and drilling out the foam shin support.

The prior art also includes continuous one-piece prostheses, such as that shown in U.S. Pat. No. 5,219,364. That prosthesis offers the advantages of light weight and improved energy storage and release characteristics. Because of its design, however, this prosthesis can require multiple patient trips to the prosthetist for fitting. In certain cases the patient may have to be fitted with another prosthesis which will be adjusted for various parameters, including height, pylon length, inversion, and eversion. Once the prosthesis is adjusted, the measurements from the adjusted prosthesis are then used to form the one-piece prosthesis, following a time consuming process. Further, once the prosthesis is manufactured, adjustments may require reheating and reforming the prosthesis.

U.S. Pat. No. 5,993,487 discloses a prosthetic component for use in a human lower limb prosthesis. The component consists of an preformed integrated pylon-keel or foot component. In practice, the prosthetist would perform a stump measurement on the amputee to determine the overall height of the prosthesis from which the pylon length could be determined, then cut a preformed integrated pylon keel prosthesis to fit the pylon to an adjustable tube clamp, whereby the clamp itself is secured to the socket. Then the prosthetist adjusts the tube clamp for inversion eversion, foot position, and rotation, then the integrated pylon/keel is attached to the tube clamp and the apparatus is covered with plastic. However, this is not a complete prosthesis, but merely the pylon/keel assembly. Further, the invention requires the use of an adjustable tube clamp attached to the socket. This additional component adds complexity and weight to the structure. Moreover, because the keel and pylon are an integrated unit, an inventory that could allow for the naturally occurring variety of needed keel sizes and pylon lengths would require an extremely large assortment of integrated keel/pylon units.

It would be advantageous to provide an improved method and prosthesis therefor that avoids the problems associated with the prior art. It would further be advantageous to provide a lightweight modular prosthesis and a method of assembly therefor that can be assembled in a single sequence of steps, maximizing simplicity and minimizing the time expended by the wearer in achieving an acceptable fit.

SUMMARY OF THE INVENTION

The difficulties associated with the prior art are overcome by providing an improved prosthetic component and method for assembly wherein the prosthesis comprises prefabricated modular components including a socket adapter, shank or pylon, a keel, and a foot. The method for preparation of the improved prosthesis reduces the time required for prosthesis preparation over that of the prior art, and includes the steps of making a cast of the remaining leg stump and forming a socket therefor; placing the socket in an alignment jig; selecting and assembling a prefabricated keel, pylon, and socket adapter; shaping the socket adapter to a desired configuration; attaching the socket adapter to the socket; draping a final coating of copolymer on the interior pieces, and removing the pylon and socket adapter. There is a single method of adjustment of the prosthesis, which is accomplished by presetting the position of the foot prior to attaching the socket adapter/pylon/keel to the socket. The connecting face of the socket adapter is shaped to incorporate the proper alignment between the socket and the keel, and the length of the pylon is selected to provide the proper length of the prosthesis. The approximate fabrication time for this method is less than one hour, which is a substantial time savings per unit. Because of the reduced preparation time, should the prosthesis prove unsatisfactory, which is common in prosthesis manufacturing, making another prosthesis results in much less wasted man hours.

A solid cast of the residual stump is made in a standard method. When making this cast, a hollow tube or pipe is put in the cast, which provides a basis for vacuum forming a polymer socket over the cast. The socket is allowed to cool and harden, and the plaster is removed. After this, another pipe is held in a correct position in the socket, and a new cast is poured using the socket as a mold.

The socket is supported by the pipe and set up in a support jig until proper orientation is achieved. This can be achieved by aligning and bending the metal pipe to a proper orientation. After this, the appropriate keel, pylon, and socket adapter are selected and assembled under the properly oriented socket. The components are glued to each other, and the assembled keel/pylon/socket adapter is then placed in the correct orientation to the socket and bonded to the socket using rigid foam.

The unit is then removed from the alignment jig, and a majority of the socket is cut away from the cast. The cast then receives any desired modifications. The final coating of copolymer is then applied to the unit, shaped, and allowed to cool and harden. After this step, the pylon, socket adapter, and socket are removed from the shell, and the socket is then returned to the shell and secured. The foot is then glued to the keel.

BRIEF DESCRIPTION OF THE DRAWINGS

The detailed description is best understood by reference to the following figures, in which.

DETAILED DESCRIPTION OF THE INVENTION

Figure 1:
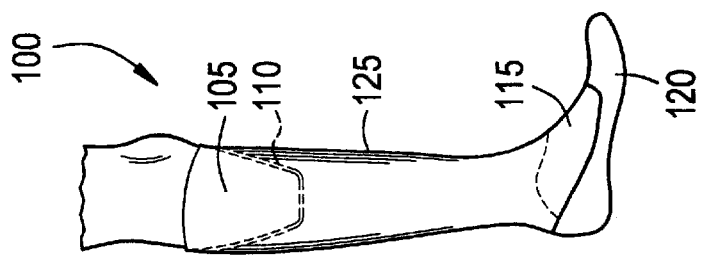
FIG. 1 is a side elevational view of a typical lower leg prosthesis.

Referring first to FIG. 1, a prosthetic device 100 is illustrated. The preferred prosthetic device is designed to replicate certain functional aspects of the human leg, especially for lower limb amputees. The prosthetic device 100 is configured to fit over a residual stump 105 of a limb. The preferred adaptation is with a socket 110, which is made to ultimately conform to the shape of the stump 105. At the lower end, the keel 115 replicates the structure of the foot, and generally has a foot prosthesis 120 of suitable shape attached to further imitate the appearance and functional characteristics of a human foot. The shank 125 of the prosthesis is a generally vertical component functioning to transmit forces between the residual limb, or stump, of the amputee and the keel 105.

Figure 2:
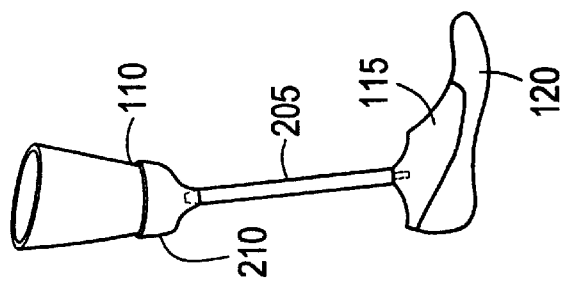
FIG. 2 is a side elevational view of a semi-completed prosthesis, including intermediate components used in an embodiment of a method of the present invention.

During the fabrication of a prosthetic device, intermediate components are needed prior to the final draping, or drop, of the exterior of a prosthesis. FIG. 2 is a side elevational view of intermediate components used in an embodiment of a method of the present invention. In this view, the keel 115 and foot 120 portions are already assembled together. Projecting from the keel 115 is a pylon 205, which longitudinally fixes the keel from the socket 110. Topping the pylon 205 is a socket adapter 210, which adapts the pylon 205 to the socket 110. The socket 110 is made to conform to the residual stump 105 of the patient. This socket 110 is also referred to as a cup, which becomes more apparent toward the end of the assembly procedure when it is trimmed to height of only a few inches. This socket 110 will be removed from the interior of the prosthesis 100 at the same time as the pylon 205 and socket adapter 210, but it will be replaced and secured in the prosthesis 100 following removal of the pylon 205 and socket adapter 210.

The pylon 205 is shown with a square cross section, but any cross section that provides suitable strength may be used. Additionally, the pylon 205 can be hollow or solid. However, since one of the benefits of this invention is to enhance ease and speed of assembly, the shape should be that which enables simple fabrication and handling of the pylon 205.

Figure 3:
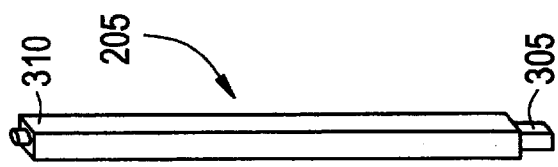
FIG. 3 is side view of a pylon according to an embodiment of the present invention.

In FIG. 3, the pylon is shown in isolation. It is shown with a square cross section, which facilitates production. The diameter of the pylon is sized to fit inside the shank of the prosthesis, preferably on the order of approximately one inch. One end 305 of the pylon 205 is smaller than the general diameter of the pylon, approximately ⅞ inch, so that it can fit into a similarly sized female hole in the keel 115.

Figure 4:
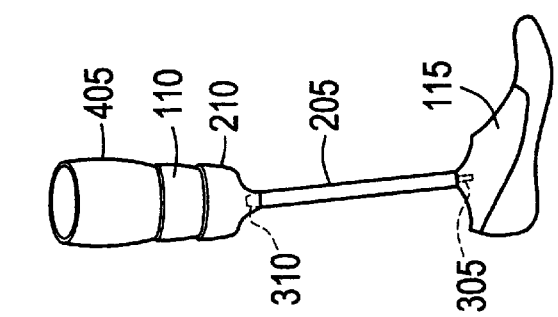
FIG. 4 is a elevational view of a semi-completed prosthesis, including intermediate components used in an embodiment of a method of the present invention.

The opposite end 310 is not so sized, and therefore may fit into an approximate one inch female hole in the socket adapter 210, and may be cut down in length without affecting its fit. FIG. 4 shows the reduced end 305 and the opposite end 310 of the pylon in an assembled position between the socket adapter 210 and the keel 115.

A complete method according to an embodiment of the present invention for production of a prosthesis is hereinafter described.

Cast Preparation for Initial Drop

An exterior negative cast of the stump is made in any standard manner. This can be accomplished by surrounding the stump with plaster of Paris, allowing the mold to dry, and carefully removing the negative mold from the stump. This negative mold is then filled with plaster to create a mold of the stump. A hollow metal pipe, which will be the primary conduit for applying vacuum for the initial drop, is placed in the plaster extending outward. After drying, the exterior negative mold is removed, leaving a positive cast of the stump with the hollow pipe extending therefrom.

Two small holes are drilled in the pipe within 1.5 inches from top of the cast. The holes are then covered with screen to allow air evacuation, and to prevent the later-applied plastic from sealing off the holes. The top of the cast is covered with Dacron felt adhered with spray adhesive. The cast is placed in a vise and a vacuum hose is connected to the pipe. At this point, the popliteal should be faced down towards the floor.

Preferably, ⅛-inch thick copolymer plastic is used to fabricate the socket 110, which is shown in FIG. 2. Copolymer of natural or any flesh tone color can be used for this socket as long as is consistent with between $9^0/_{10}$ and $9^3/_7$ ratio of polypropylene and polyethylene.

A plastic sheet is cut to a width six inches greater than the circumference of stump, and a length of six inches longer than the length of the socket. The plastic is cleaned and deburred, and aligning marks made on the center of bottom and top of plastic with a marker, which will aid in centering the plastic over the cast when molding.

The plastic is then placed in the oven at an appropriate temperature to render it pliable. This will vary depending on the particular plastic composition, but is generally around 400° F. The required heating time will vary according to thickness of the plastic, but will generally be between 8–24 minutes. Immediately prior to removal of the plastic from the oven, nylon knee high panty hose material is saturated with silicone oil and pulled over the case with the seam placed laterally to medially on the distal end. The nylon stocking functions to maintain air passages along the surface of the cast. These air passages reduce the changes of bubbles forming in the socket by pockets of air trapped between the copolymer sheet and the pipe assembly and hence allow a more definite conformance of the copolymer sheet to the cast. Further, the nylon stocking aids in removing the socket from the case. The plastic is removed from the oven when appropriate and is aligned over the center of the case using the previously made marks. The plastic is carefully draped while avoiding any stretching or drooping, and is manually sealed around the case and pipe to ensure tightness of the vacuum, which should be pulling between 10 and 20 pounds of pressure. The seam of the plastic is trimmed ¼-inch and the distal end of the seam is rolled with a 1-inch dowel rod for a smoother distal end cap.

The plastic is allowed to cool for approximately 15 minutes and is then removed from the cast using the following method. The plastic is cut with a cast saw around the entire superior edge of the socket. The socket is then removed from the cast by either blowing it off or by the conventional method of breaking out the cast. Socket removal by air pressure is preferred for casts conical in shape and without prominent undercuts. For this method, a small hole is drilled through the distal end of the socket and liner. The positive model is secured in a vise, and a nozzle of an air pistol is placed against the hole. When pressure is applied, the socket should pop off the cast. Tapping of the superior rim of the socket with a hammer against a block of wood may be used in stubborn cases.

The proximal edge of the socket is trimmed flat, and the distal end of socket is then prepared for foaming by using a router to roughen the area that will be contacting the socket adapter.

Pouring the Socket

The inside of the socket, which will now function as a mold for another plaster cast, is lightly powdered. Marks are made mid line on the lateral side of the socket and mid line on the posterior aspect of socket.

A hollow metal pipe is positioned to extend to at least 16 inches from the top of the socket. The socket is positioned to be filled vertically on a level surface in 1 degree of flexion (the crest of the tibia is the guideline for this). The pipe is centered in the socket and aligned to the center lateral and posterior lines previously marked on the socket. The pipe should also be positioned in the center of the socket as well as being perpendicular to the flat surface that the socket is on. A small level may be used to achieve this. The new plaster cast is slowly poured, maintaining the pipe position, and allowed to set up.

Aligning Socket in Vertical Jig

A collar (not shown) is temporarily placed on the pipe approximately three inches from the top. The socket is placed in a vertical jig and checked for alignment so that the socket's popliteal area is parallel to the line of progression. At this point, if the abduction or adduction is not correct the pipe is bent until corrected, then the unit is remounted in the jig. It is important to make adjustments one at a time until the correct alignment is achieved.

The center of the patella tendon is marked on the socket so that the patella tendon line is the same height to the base of the vertical jig as the anatomical height of the patella tendon recorded from the patient's sound extremity. The distance from the bottom of the socket to the base of the vertical jig is measured, and this number minus one inch is recorded.

Assembling the Components

The foot is placed on a ½-inch heel wedge directly under the socket, which is being held in the jig. The keel is inserted into the foot so that the alignment square on foot is in the square hole in keel. The pylon is then inserted into the keel, and the socket adapter placed over the other end of the pylon.

When the components are assembled but not yet glued, the length of the prosthesis from the bottom of the foot as it stands on the bench to the top of the socket adapter is measured. The previously recorded measurement taken from bottom of the socket to the base of vertical jig is subtracted from the prosthesis length. The remainder is cut off the length of the top of the pylon after removing the socket adapter. The components are reassembled and placed under the socket on the vertical jig base with the ½-inch heel wedge in place. At this point, there should be approximately ¼ inch between the bottom of the socket and the inside of the socket adapter.

The components are disassembled and both ends of the pylon are lightly sanded where they fit into the keel and socket adapter. The inside of the well on the socket adapter is roughed up with a cone on the router, which will ensure good bonding between the distal end of the socket and the inside of the socket adapter. A small amount of 10-minute epoxy is used to bond keel and socket adapter to the pylon.

Aligning and Attaching Assembled Components to the Socket

The assembled components are placed under the socket with the ½-inch heel wedge in place. The foot is then turned to achieve correct toe out. The mid center lateral line is aligned so it is in alignment to the point where the lateral corner of the keel and pylon meet. A ruler or plumb line are helpful in this regard. The posterior mid line previously marked on the socket is aligned so that the point where the pylon inserts into the keel is ½ inch medially to the socket. This should be done while still maintaining the correct toe out.

Bonding the Components to the Socket

After alignment is achieved, the foot is secured and a small amount of rigid foam is slowly poured into the well of the socket pylon adapter. The foot should not be released until the foam starts to solidify. The foam should be allowed to harden before moving the unit.

Preparing for Final Drop

The prosthesis is removed from the vertical alignment jig. The area where the plastic socket begins an inward flair on the distal end is located; some foam might have to be removed to find this position. On each of the medial and lateral sides a dowel hole (not shown) is drilled at a 45-degree angle through the plastic into the case approximately one to two inches in depth.

The socket is then split medially using the cast saw to remove the socket from the cast. Sometimes a lateral split is needed as well. The socket should not be cut within one inch of the dowel holes.

At this time the semi-completed prosthesis can be checked on a level surface, with the heel wedge in place or in the shoe. If changes are needed, the pylon is heated and manipulated as necessary. If linear changes are required the pylon can be cut (usually at the thickest part of the socket adapter), moved as necessary and rebonded with 10-minute epoxy.

Preparing Distal End and Finalizing

A cast saw is used to cut through entire socket, at the distal end approximately ¼ inch above the dowel holes. The part of the socket that remains is referred to as a cap. The outer edge of the cap is then sanded to a thickness of 1/32 inch at its proximal edge. Two 5-inch dowels (3/16-inch diameter) are cut and one end of each is sharpened to a point in, for example, a pencil sharpener. With the cap replaced on the cast, the holes are aligned and the dowels can be gently tapped through the cap into the cast until they bottom out. The dowels are cut flush and the ends mushroomed to hold the prosthesis on the cast.

At this time the cast above the distal end cap may be modified as needed, for example, for fibula head relief or distal tibia.

FIG. 4 shows a semi-completed prosthesis that has been prepared for the final drop. The plaster cast 405 is clearly visible in the cap or socket 110, which has been cut down according to the above steps.

The cast is placed in a horizontal position and plaster is used to smooth any irregularities and transitions in the foam. The plaster should be allowed to dry before lightly sanding.

Preparation for vacuum forming includes drilling two small holes in the pipe as close to the top of the cast as possible. These holes are covered with two layers of sanding screen and taped in place. For the final drop, 3/16-inch plastic is cut to the following measurements: top width= circumference+6 inches; bottom width=15 inches; length= prosthesis length+6 inches.

The plastic is cleaned and deburred and the center of the top and bottom are marked to assist in centering plastic during the drop.

To assist the eventual removal of the inner foam core, the following procedure is used. Using clean dry panty hose, the toe is tied in a knot and the excess is cut away. The panty hose is placed over a model with the knot kept in the center portion of the proximal keel. Once in place a piece of aluminum foil large enough to encircle the pylon from just below the top of the cap to within 1 inch of the base of the keel is pressed around the pylon and the excess removed. Over this is placed another nylon in the same manner as above. A plastic bag is pulled over the entire model and vacuum applied. This assists in removal of wrinkles from the foil. The bag is then removed.

A small indentation in the center lower portion of the base of the keel is created using an awl. Secondary vacuum is connected by pushing a metal vacuum rod tip into the indentation. A thin strip of Dacron felt interlaced with screen is attached to the rod to prevent the air vacuum from being sealed off.

A reinforcement strut of ¼-inch×3/16-inch copolymer can be added to the prosthesis for additional strength, if needed. It is put in place at the same time as the initial drop, and runs the anterior length of the prosthesis from one inch above the distal tibia to center of the dorsum of the keel.

Once the plastic has heated to temperature, the vacuum is turned on. The heated plastic is removed from the oven and positioned over the prosthesis from near the top of the cast to the keel, aligning center marks on the center of the prosthesis. The plastic is allowed to conform to the contours. Once the vacuum has sealed the plastic, the posterior seam is cut within 1 inch of the prosthesis. A cut is then made perpendicular to and through the seam on the underside of the primary pipe, and the secondary pipe is tied off with nylon cord.

Figure 5:
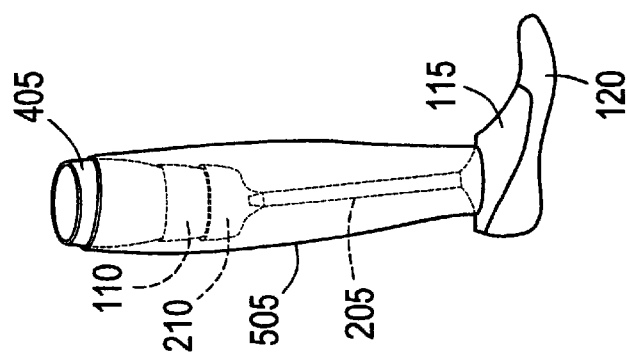
FIG. 5 is side elevational view of a nearly completed prosthesis, including intermediate components used in an embodiment of a method of the present invention.

FIG. 5 is side elevational view of a nearly completed prosthesis, including intermediate components used in an embodiment of a method of the present invention, and shows the final polymer coating 505 over the supporting structure, which includes the cast 405, the socket 110, socket adapter 210, pylon 205, and keel 115. The foot 120 is show for reference purposes; it gets permanently attached during the next step.

Preparing the Prosthesis for Bonding of the Foot

Once the plastic has cooled for at least 20 minutes, it is disconnected from the primary and secondary vacuums. A cast saw is used to cut around the perimeter of the socket above the trim lines exposing the plaster, which is then chiseled out. A belt sander can be used to reduce the posterior seam to the appropriate size considering patient weight and activity level. The posterior seam should generally be rounded and reduced to 1/32 inch at the top of the popliteal area. On heavier or more active patients the seam is preferably at least ¼ inch.

The plastic on the bottom of the keel is removed using the belt sander to expose the two raised segments of foam. The periphery and the apex of the keel are then roughened with a 36-grit cone on low speed.

A rounded edge 7/8-inch spade bit is used to drill through the keel at the dimple on the bottom until the space in the keel where the pylon inserts into the keep is reached. Epoxy on the base of the pylon should be visible at this point. A ½-inch solid pipe can be used in this hole to drive the foam pylon, socket adapter and cap from the prosthesis through the inside of the socket. The foam in the base of the keel is then hollowed out using a small acorn bit. It is important too that the diameter of the hole created by the spade bit is kept as small as possible. A screwdriver may assist in removal of the foam. The excess foam is removed from the cap and the cap replaced in the prosthesis and is wet-glued in place using a barge cement.

The "skin" is removed from the bottom of keel and a cross pattern of cuts no deeper than 3/32 inch is made on all exposed surfaces on the keel bottom.

Bonding the Foot

With the foot on prosthesis and the assembly on a ½-inch heel wedge the foot and prosthesis are held firmly in place. The area around the rubber flange encircling the keel is marked and the foot removed. Methyl ethyl ketone is used to wipe the foot clean, particularly in the well area, and the foot is allowed to dry.

Epoxy is applied between the foot and the prosthesis, and the assembly is placed in a bag and vacuum attached. With the toe flat on the work surface, the epoxy is allowed to cure.

The above method may also be adapted for transferring a fitting prosthesis. In this option, a piece of natural copolymer is attached to the base platform of the vertical alignment jig. The prosthesis that is to be transferred is centered on the platform with a ½-inch heel wedge under the heel, and the socket is poured using a pipe with a collar attached and inserted in the jig. After the plaster has hardened the outline of the foot is traced on the plastic platform. The height of the collar as it is attached to the main strut of the vertical alignment jig is noted, the prosthesis is removed from the jig, and the socket is removed from the cast. The socket is dropped in ⅛-inch copolymer and then the complete method above is employed. The alignment must be lengthened ½ inch from the height at which it was poured.

While the above detailed description describes the preferred embodiments of the present invention, it will be understood that the present invention is susceptible to modification, variation and alteration without deviating from the scope of the fair meaning of the subjoined claims.

What is claimed is:

1. A method for constructing a prosthesis for placement on a remaining stump of a human limb, comprising the steps of:

making a cast of the remaining stump and forming a socket therefor;

selecting appropriate prefabricated modular components including at least a keel, a pylon, and a socket adapter;

assembling said prefabricated components;

adjusting a relative angle between said socket and said keel;

attaching said socket adapter to said socket;

draping a coating of copolymer over said assembled keel, pylon, socket adapter, and socket; and removing said pylon and socket adapter from an interior of said coating of copolymer by providing an access to an interior of the prosthesis by way of said keel and forcing said pylon and socket adapter through an opening in said socket.

2. The method of claim 1, wherein the step of assembling said prefabricated components comprises gluing said components together.

3. The method of claim 2, wherein the step of adjusting the relative angle between said socket and said keel is accomplished by selecting a desired angle and attaching said socket adapter to said socket so as to achieve and maintain said angle.

4. The method of claim 3, further comprising an additional step of readjusting the relative angle by cutting said socket adapter into two pieces, repositioning said pieces relative to one another, and reconnecting said pieces.

5. The method of claim 3, wherein said copolymer is a substantially homogeneous blend of between 7 and 10 percent polyethylene, the remainder being polypropylene.

6. The method of claim 5, wherein said human limb is a leg.

7. The method of claim 6, wherein said leg is a lower leg.

8. The method of claim 1, further comprising the step of preparing at least said pylon for subsequent removal from interior of said prothesis prior to draping said coating of copolymer over said assembled keel, pylon, socket adapter and socket.

9. The method of claim 8, wherein said step of preparing at least said pylon for subsequent removal includes covering said pylon with at least one layer of aluminum foil.

10. The method of claim 9, wherein said aluminum foil is vacuum formed against a surface of said pylon.

\* \* \* \* \*